United States Patent [19]

Niemi et al.

[11] Patent Number: 5,782,233
[45] Date of Patent: Jul. 21, 1998

[54] METHOD AND ARRANGEMENT FOR IDENTIFYING AN EXISTING CONNECTION IN APPARATUS FOR THE VENTILATION OF A PATIENT

[75] Inventors: Hannes Niemi; Markku Hyvönen, both of Espoo, Finland

[73] Assignee: Instrumentarium Oy, Helsinki, Finland

[21] Appl. No.: 565,349

[22] Filed: Nov. 30, 1995

[30] Foreign Application Priority Data

Nov. 30, 1994 [FI] Finland ................................. 945649

[51] Int. Cl.⁶ .................................................. A61M 16/00
[52] U.S. Cl. ........................ 128/202.22; 128/203.12; 128/203.14; 128/205.13
[58] Field of Search .................. 128/202.22, 203.14, 128/203.15, 203.12, 205.13, 204.22, 205.14, 204.23, 203.28, 205.24, 205.23, 204.24, 207.12, 202.27

[56] References Cited

U.S. PATENT DOCUMENTS

| | | | |
|---|---|---|---|
| 4,020,834 | 5/1977 | Bird | 128/205.14 |
| 4,155,357 | 5/1979 | Dahl | 128/202.22 |
| 4,444,201 | 4/1984 | Itoh | 128/204.23 |
| 4,766,894 | 8/1988 | Legrand et al. | 128/204.21 |
| 5,119,810 | 6/1992 | Kiske et al. | 128/204.22 |
| 5,320,093 | 6/1994 | Raemer | 128/203.12 |
| 5,471,977 | 12/1995 | Olsson et al. | 128/204.22 |
| 5,497,767 | 3/1996 | Olsson et al. | 128/205.14 |
| 5,509,406 | 4/1996 | Koek et al. | 128/203.14 |
| 5,522,381 | 6/1996 | Olsson et al. | 128/203.12 |

FOREIGN PATENT DOCUMENTS

| | | | |
|---|---|---|---|
| 246121 | 11/1987 | European Pat. Off. | A61M 16/00 |
| 2596518 | 10/1987 | France | A62B 18/08 |
| WO 86/05992 | 10/1986 | WIPO . | |
| 90/03820 | 4/1990 | WIPO | A61M 16/00 |
| 91/03979 | 4/1991 | WIPO | A61B 5/08 |

*Primary Examiner*—Vincent Millin
*Assistant Examiner*—V. Srivastava
*Attorney, Agent, or Firm*—Andrus, Sceales, Starke & Sawall

[57] ABSTRACT

A method and arrangement in connection with the ventilation of a patient, wherein the lungs of the patient are ventilated mechanically by means of a ventilator or manually by means of a reservoir bag as the patient's own respiratory activity is insufficient or totally prevented. In order to eliminate a faulty connection, the behaviour of the pressure or the flow in the patient circuit, in the circuit associated with the ventilator or in the circuit associated with the reservoir bag is monitored in connection with ventilation and the obtained information is compared with the desired operation.

27 Claims, 4 Drawing Sheets

METHOD AND ARRANGEMENT FOR IDENTIFYING AN EXISTING CONNECTION IN APPARATUS FOR THE VENTILATION OF A PATIENT

BACKGROUND OF THE INVENTION

1. Field of the Invention

The present invention relates to a method for identifying an existing connection in apparatus for the ventilation of a patient, wherein the lungs of the patient are ventilated mechanically by means of a ventilator or manually by means of a reservoir bag as the patient's own respiratory activity is insufficient or totally prevented. The present invention also relates to an arrangement for identifying an existing connection in apparatus for ventilation.

2. Description of the Related Art

The ventilation of a patient is a normal procedure for instance during anaesthesia. In ventilation performed mechanically, an apparatus, i.e. a ventilator, handles the ventilation and in manual ventilation, a person belonging to the medical staff handles the ventilation by means of a reservoir bag.

There are different types of ventilators. A typical ventilator using pressurized gas as a driving force comprises a control unit, a bellows unit and a patient circuit. The task of the control unit is to implement control parameters characterizing lung ventilation, such as batch volume, respiratory frequency, the relation between inhalation and exhalation periods, and inhalation pause. The bellows unit using pressurized gas as a driving force separates the control unit and the patient circuit of the ventilator from each other. The task of the bellows unit is to prevent the mixing of a patient's respiratory gases and the driving gas. The ventilator discussed above is described in more detail in U.S. Pat. No. 5,400,499.

The task of the patient circuit is to provide separate routes for inhalation and exhalation gases to and from the patient and to remove carbon dioxide from the exhalation gases.

The reservoir bag used in manual ventilation is usually a bag made of rubber material, which is connected to the patient circuit in such a manner that the ventilation of a patient can be carried out by squeezing the reservoir bag manually to a suitable extent and at a suitable frequency.

In many known apparatuses, the ventilator and the reservoir bag are connected to the patient circuit by means of a three-way valve in such a manner that a shift from mechanical ventilation to manual ventilation or vice versa can be quickly performed when a shift is considered to be necessary. In the above-mentioned connection, for instance three tubes are connected to the three-way valve, one of which tubes extends to the patient, another to the reservoir bag and the third to the ventilator. It is essential that the tubes are connected correctly, since if they are connected in a faulty manner, the situation is dangerous as regards the patient. If the tubes are connected in a faulty manner and the ventilation is set to mechanical ventilation mode, the ventilator is actually connected to the reservoir bag. Fresh gas connected to the patient circuit increases the pressure of the patient circuit simultaneously for instance to the level of an adjustable pressure valve, etc. During manual ventilation in a normal situation, the pressures of the patient circuit and the manual ventilation branch rise when the reservoir bag is squeezed, and the pressure of the manual ventilation branch is higher than the pressure of the patient circuit when the reservoir bag is squeezed. If the tubes are connected faultily in an arrangement where meters are arranged in a fixed manner in the three-way valve, the pressure of the patient circuit rises in an inhalation situation but the pressure of the manual ventilation branch of the valve remains, however, lower than the pressure of the patient circuit when measured in the three-way valve. The expression "in a fixed manner in the three-way valve" refers to the fact that the meters do not move with the tubes, whereby it is possible to connect for instance a bellows tube to a passage intended for a patient circuit tube. In such a case, a meter intended to indicate the pressure of the patient circuit actually indicates the pressure of the manual ventilation branch. In mechanical ventilation, at the inhalation stage, the pressure of the patient circuit increases in a normal manner, and the pressure of the manual ventilation branch should remain essentially even, even if slight leakage may occur. If the tubes are connected in a faulty manner, the compression of the bellows of the ventilator causes gases to be passed into the reservoir bag, the pressure measurement value of the patient circuit being increased simultaneously if the meters are arranged in a fixed manner in the three-way valve as described above. Due to the fresh gas flow, the pressure measurement value of the manual ventilation branch increases. At the exhalation stage, the pressure measurement value of the manual ventilation branch increases further.

The problem presented above is known in the field, and attempts have been made to eliminate mistakes by means of the systematic operation of the staff, that is, the connections are checked for instance in daily inspections. In addition, such tubes and connectors are used that a faulty connection of tubes is not possible since the connectors match only if the tubes are connected correctly. In practice, it has been impossible to eliminate the mistakes, however, since even after the daily inspections mentioned above it is possible to detach tubes and rearrange the system for one reason or another. Such a situation arises for instance when a patient changes, i.e. is replaced by another. It should be noticed that the prevention of a faulty connection by means of tube connectors is not a safe manner of proceeding, since hospitals often use their own tubes and it is always possible to come by connectors with which a faulty connection could be made. The possibility of mistakes is increased by the hurry and the stress of the staff, which often occur in hospitals.

SUMMARY OF THE INVENTION

The object of the invention is to provide a method by means of which the disadvantages of the prior art can be obviated. This is achieved with the method of the invention, characterized by monitoring in connection with ventilation the behaviour of the pressure or the flow in the patient circuit, in the circuit associated with the ventilator or in the circuit associated with the reservoir bag and comparing the obtained information with the desired operation. The arrangement of the invention is characterized in that the patient circuit, the circuit associated with the ventilator or the circuit associated with the reservoir bag is provided with a meter, which is arranged to measure during ventilation the behaviour of the pressure or the flow in the patient circuit, in the circuit associated with the ventilator or in the circuit associated with the reservoir bag, and that said arrangement is further provided with means for comparing the obtained information with the desired operation.

The main advantage of the invention is that faulty connections can be detected in all situations very quickly. Errors can also be detected during operation. This has a great significance for instance in situations where a patient changes. A further advantage is the simplicity of the invention, the implementation and use of the invention being thus advantageous.

BRIEF DESCRIPTION OF THE SEVERAL VIEWS OF THE DRAWING

In the following, the invention will be described in more detail by means of the preferred embodiments shown in the accompanying drawing, in which.

DETAILED DESCRIPTION OF THE INVENTION

Figure 1:
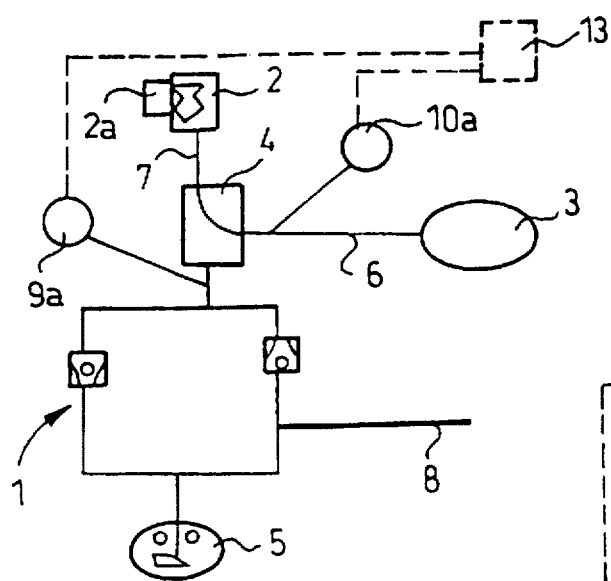
FIG. 1 shows schematically the use of an arrangement of the invention in connection with a faulty connection.

FIG. 1 shows a system applying the method of the invention as a schematic diagram. Reference numeral 1 indicates a patient circuit, reference numeral 2 a ventilator used in mechanical ventilation, and reference numeral 2a the control unit of the ventilator 2. Reference numeral 3 indicates a reservoir bag used in manual ventilation. Reference numeral 4 indicates the three-way valve used in this application, by means of which the patient circuit 1, the ventilator 2 and the reservoir bag 3 are connected to one another. Reference numeral 5 indicates a patient in FIG. 1, and reference numeral 6 a tube by means of which the reservoir bag 3 is connected to the three-way valve 4. In FIG. 1, reference numeral 7 indicates a tube or a passage by means of which the ventilator 2 is connected to the three-way valve 4. Reference numeral 8 indicates a fresh gas connection connected to the patient circuit 1.

During anaesthesia, the patient is ventilated either mechanically by means of the ventilator 2 or manually by means of the reservoir bag 3. The structure and operation of the details presented above and the ventilation of a patient in general represent known prior art to one skilled in the art, wherefore these matters are not dealt with in more detail in this context.

In ventilating a patient, it is essential that the ventilation system operates in a desired manner in every situation. Desired functions are inspiration into the patient and expiration. The user generates the desired functions in manual ventilation and the ventilator 2 generates them in mechanical ventilation. An unequivocal response corresponds to both desired functions in a system connected correctly, and correspondingly, a different unequivocal response corresponds to both desired functions in a system connected faultily, i.e. a certain response always corresponds to a certain function, it being possible to measure this response in different parts of the equipment. To determine the actual performance of the system, a measurement and, correspondingly, information on what the desired function is in that situation are required.

The desired inspiration function in manual ventilation is that gas flows into the patient when the reservoir bag 3 is squeezed. In squeezing the reservoir bag 3, i.e. at the inspiration stage of manual ventilation, the objective is that gas flows into the lungs of the patient and that the pressure rises in the patient circuit. By measuring the pressure or the flow in the patient circuit and comparing the obtained information with the desired function, i.e. with inspiration in this case, it can be observed whether or not the operation has been successful. By measuring the pressure in the ventilator branch, it can be observed that the desired function has been achieved when no pressure and/or flow is present in the ventilator branch.

The desired expiration function in manual ventilation is that gas flows out of the patient when the hold on the reservoir bag 3 is slackened. When the reservoir bag 3 is released, i.e. at the expiration stage of manual ventilation, the objective is that gas flows out of the patient and that the pressure decreases in the patient circuit. By measuring the pressure and/or the flow in the patient circuit it can be concluded whether the desired function has been achieved.

The desired inspiration function in mechanical ventilation is the same as in manual ventilation, but the compression of the reservoir bag 3 is replaced by an apparatus, i.e. the ventilator 2. The apparatus is thus aware of the desired function.

The desired expiration function in mechanical ventilation is the same as in manual ventilation. The pressure release of the driving gas section corresponds to the release of the reservoir bag 3. Also in this situation, the apparatus is aware of the desired function.

In connection with the application described above, it is possible that dangerous situations occur relating to the three-way valve 4, since it is possible that a connection is made in a faulty manner, whereby the equipment will not operate in the intended manner, i.e. the desired function is not produced. The faulty connection presented above is highly dangerous for the safety of a patient.

In an equipment connected correctly, the ventilator 2 and the patient circuit 1 are connected to each other in mechanical ventilation. The ventilator 2 handles the change of gases. In an equipment connected in a faulty manner, the ventilator 2 is connected to the reservoir bag 3, and the patient circuit 1 is stopped up at the valve 4. FIG. 1 shows schematically a faulty connection of the equipment presented above.

The object of the invention is to obviate the above-mentioned dangerous situations caused by a faulty connection of the tubes. As stated above, the invention is based for instance on pressure measurement and the comparison of the obtained information with a desired function, since in an equipment connected in a faulty manner the direction of the flow and the increase of the pressure are different than in an equipment connected correctly. The essential aspect of the invention is that in order to obviate a faulty connection, the behaviour of the pressure or the flow in the patient circuit 1 or in the circuit associated with the reservoir bag 3 is monitored in connection with ventilation. The expression "in connection with ventilation" means that the pressure or the flow can be monitored, according to the basic idea of the invention, during the actual ventilation and/or during the preparation for the actual ventilation. The obtained information can be compared with the desired function in many different ways. The measuring can be carried out by means of a pressure gauge 9a arranged in the patient circuit 1. The pressure can also be monitored in the patient circuit 1 or in the circuit associated with the reservoir bag 3. The circuit associated with the reservoir bag 3 is thus provided with a pressure gauge 10a, as shown in FIG. 1. In the example of FIG. 1, the fresh gas connection 8 connected to the patient circuit 1 passes more gas to the patient circuit 1. This increases the pressure of the patient circuit evenly, whereby this increase in the pressure is detected by means of the pressure gauge 9a during mechanical ventilation. By means of the pressure gauge 10a, it is possible to detect changes in pressure caused by the ventilator 2, which changes should not occur in mechanical ventilation when the gauge is connected to the reservoir bag.

It is also possible to measure the pressure difference between the circuit associated with the reservoir bag 3 and the patient circuit 1, and, in addition, the total pressure or the direction thereof in the patient circuit 1 or in the reservoir bag circuit. The measuring of the pressure/flow/pressure difference mentioned above is shown schematically in FIG. 1 by means of dotted lines. The processing of the measurement data, for instance the comparison with the desired function mentioned above, can be carried out for instance by means of a comparing unit 13, such as a logic circuit. The application presented above is not the only one possible, since the monitoring of the direction of the flow can be carried out separately by all the methods relating to flow measurement. The measurements can be carried out on different sides of the joint area, i.e. the three-way valve 4, connecting the circuit associated with the reservoir bag 3 and the patient circuit 1. The necessary variables are the pressure difference between the reservoir bag and the patient circuit, and the total pressure or the direction thereof in the circuit when manual ventilation is applied, as stated above.

Figure 2:
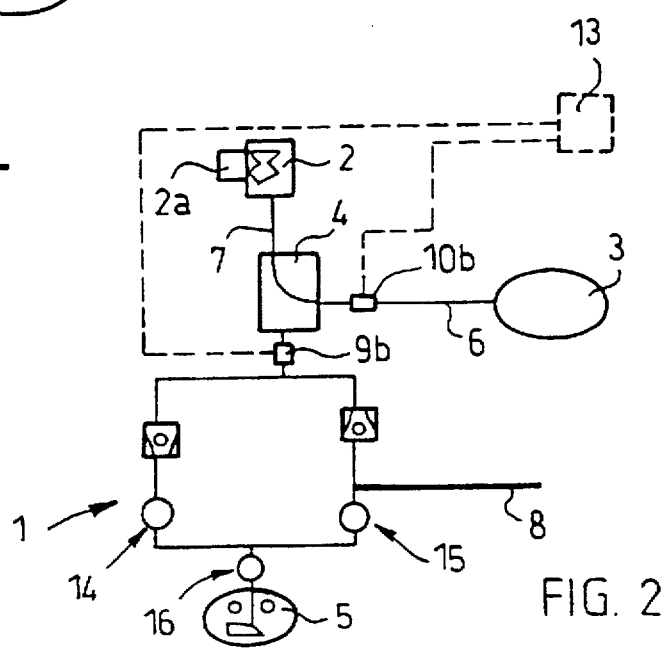
FIG. 2 shows schematically the use of a second arrangement of the invention in connection with the faulty connection according to FIG. 1.

FIG. 2 shows a situation corresponding to that shown in FIG. 1, but the difference is that in the application of FIG. 2, meters 9b, 10b measuring the flow are used instead of pressure gauges. These meters measuring the flow may be for instance conventional pressure difference flow meters or mass flow meters. The operation of the arrangement according to FIG. 2 corresponds essentially to the operation of the arrangement in FIG. 1, wherefore the above is referred to in this context.

It will be apparent that in the present invention, the location of the meters is by no means restricted to the areas shown in FIGS. 1 and 2, but the meters can also be located in a different manner. For instance the meter 9a, 9b provided in the patient circuit can alternatively also be located at areas 14, 15, 16, which are shown schematically in FIG. 2.

Figure 3:
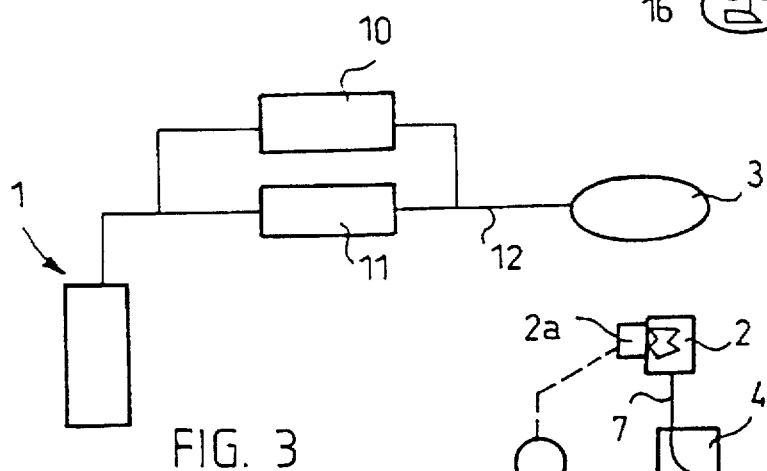
FIG. 3 shows diagrammatically a second embodiment of the method of the invention.

By means of the method of the invention, a faulty connection can also be detected during manual ventilation, since within the scope of the invention, it is also possible to use a method where the compression of the reservoir bag 3 is monitored. Only the direction of the flow is thus also needed. Such an application is shown in FIG. 3. The same reference numerals as in FIGS. 1 and 2 are used in FIG. 3 to refer to the corresponding areas. The valve 4 presented above is thus not necessary for the flow measurement, but any resistance or flow measurement method can be used. FIG. 3 shows schematically an application where a resistance 11 consists for instance of the resistance of a tube 12. The pressure is thus measured at two areas by means of pressure sensors, and the measurement results are compared. The difference between the pressures indicates the direction of the flow. However, it should be noticed that the application according to FIG. 3 can also be used in connection with such an arrangement in which the valve 4 is used. The valve 4 may thus also constitute the resistance 11.

Figure 4:
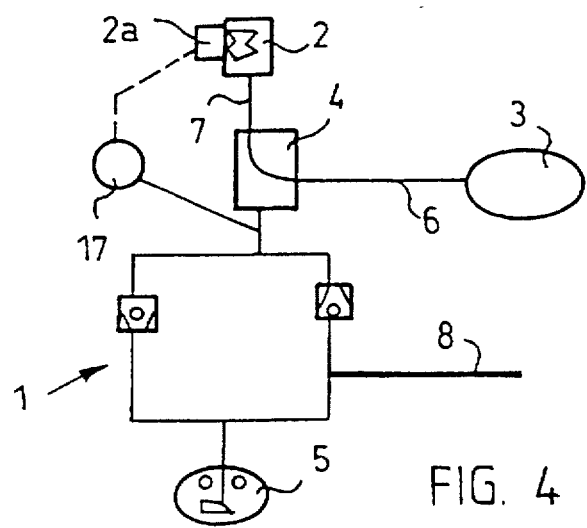
FIG. 4 shows schematically a third embodiment applying the method of the invention.

FIG. 4 shows a third preferred embodiment of the method of the invention. The same reference numerals as in FIGS. 1 and 2 are used in FIG. 4 to refer to the corresponding elements. In FIG. 4, reference numeral 17 indicates a measuring device, such as a pressure gauge, which is used for measuring the pressure in the patient circuit 1. The measuring device may naturally also be a device measuring the flow, such as a pressure difference flow meter, etc. The measuring device 17 can be arranged for instance in that branch of the three-way valve 4 which extends to the patient circuit 1. The measurement information, such as the behaviour of the pressure, obtained by means of the measuring device 17 is compared with the operation of the control unit 2a of the ventilator 2. In this application, the apparatus, i.e. the ventilator 2, is aware of the desired function. The advantage of the arrangement according to FIG. 4 is that only one pressure measurement and awareness of the ventilation are sufficient. When it is known that the ventilator has delivered or is delivering volume into the patient, this should appear in the three-way valve 4 as an increase in the pressure. If no increase in the pressure takes place in such a situation, this is due to a faulty connection.

FIGS. 5 to 12 show some applications according to the invention. In the following, the essential aspects of the examples of FIGS. 5 to 12 will be described by way of example. The functions mainly correspond to those presented in connection with FIGS. 1 to 4. The same reference numerals as in FIGS. 1 to 4 are used in FIGS. 5 to 12 to refer to the corresponding areas.

Figure 5:
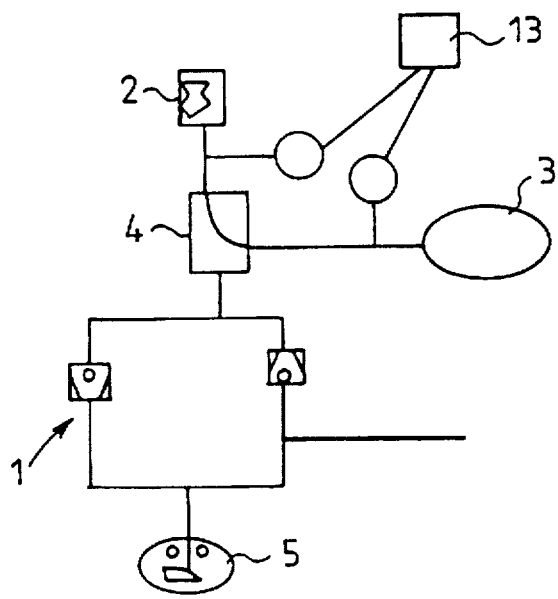
FIGS. 5 to 12 show schematically examples of different applications of the invention.

FIG. 5 shows an application in which the pressure or the flow is measured in both the circuit associated with the reservoir bag 3 and the circuit associated with the ventilator 2. The desired function is determined by measuring in both circuits. The comparing unit 13 is thus not necessary.

Figure 6:
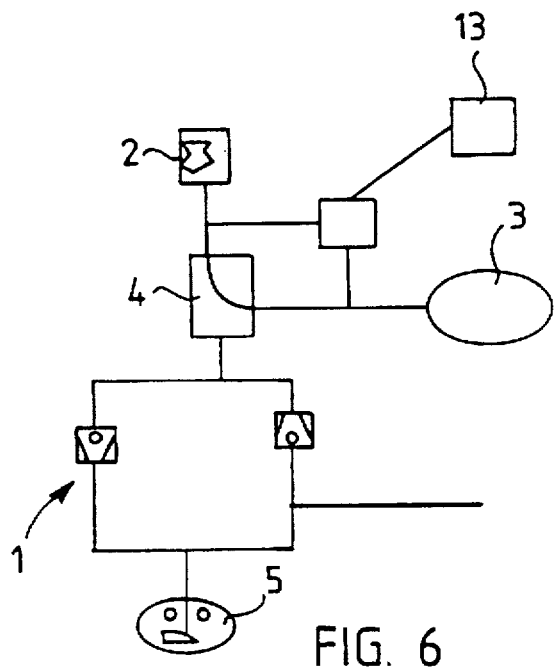

FIG. 6 shows an application in which the pressure difference is measured on different sides of the three-way valve 4 between the circuit associated with the ventilator 2 and the circuit associated with the reservoir bag 3. The comparing unit 13 is not necessary in this application either. The pressure difference provides sufficient information on the operation.

Figure 7:
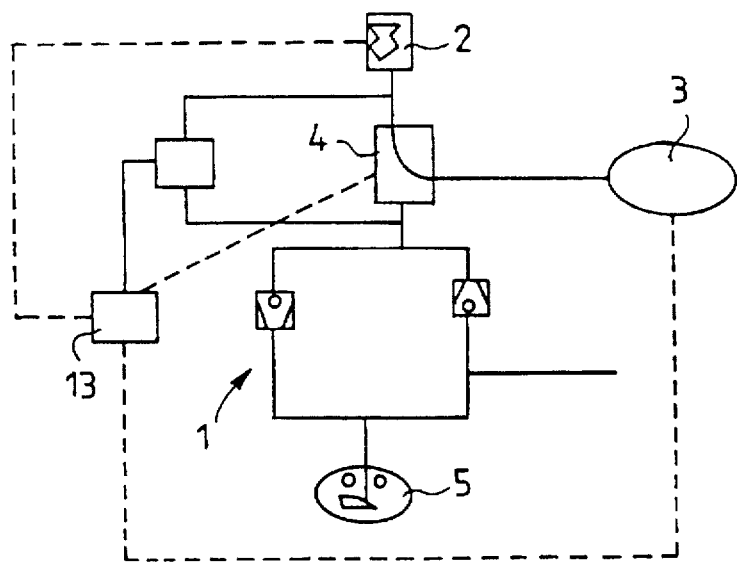

FIG. 7 shows an application in which the pressure difference in measured between the patient circuit 1 and the ventilator 2. In addition, information on whether the ventilation desired is manual or mechanical is required. This information can be obtained from the ventilator 2, the valve 4 or the reservoir bag 3.

Figure 8:
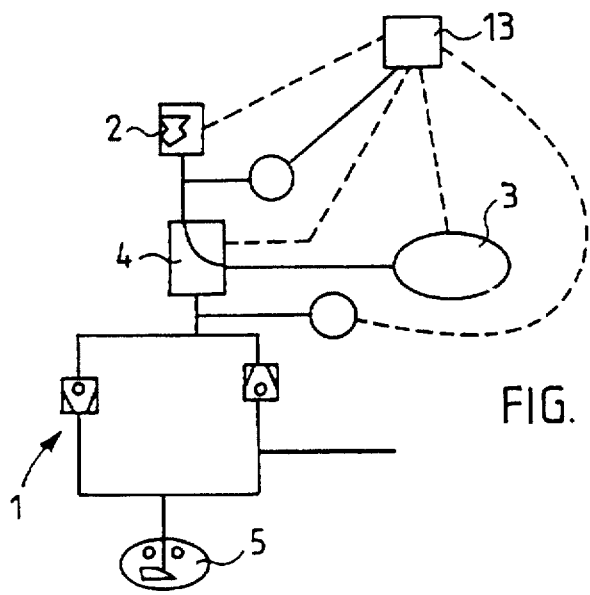

FIG. 8 shows an application in which the pressure or the flow is measured in the circuit associated with the ventilator 2 and in the patient circuit 1. In addition, information on whether the ventilation desired is manual or mechanical is required. This information can be obtained in the manner shown in FIG. 7.

Figure 9:
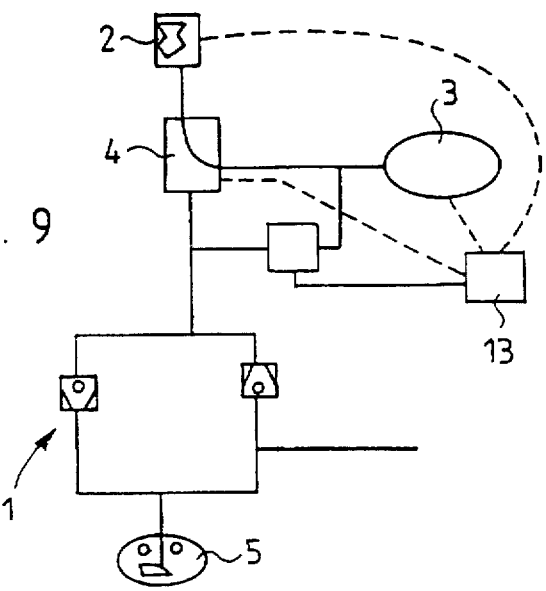

FIG. 9 shows an application in which the pressure difference is measured between the circuit associated with the reservoir bag 3 and the patient circuit 1. In addition, information on whether the ventilation desired is manual or mechanical is required here as well.

Figure 10:
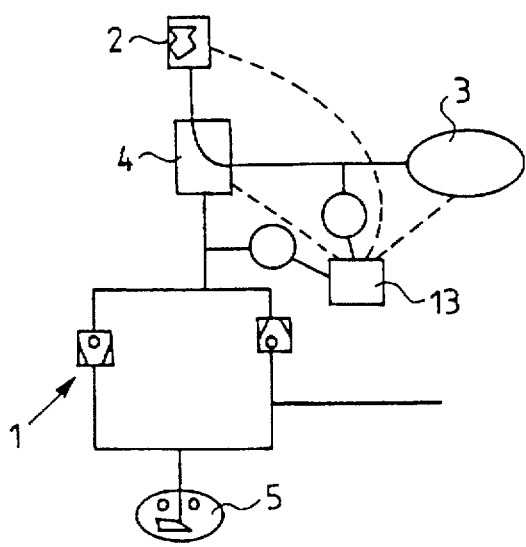

FIG. 10 shows an application in which the pressure and the flow are measured in the patient circuit 1 and the circuit associated with the reservoir bag 3. In addition, information on whether the ventilation desired is manual or mechanical is required here as well.

Figure 11:
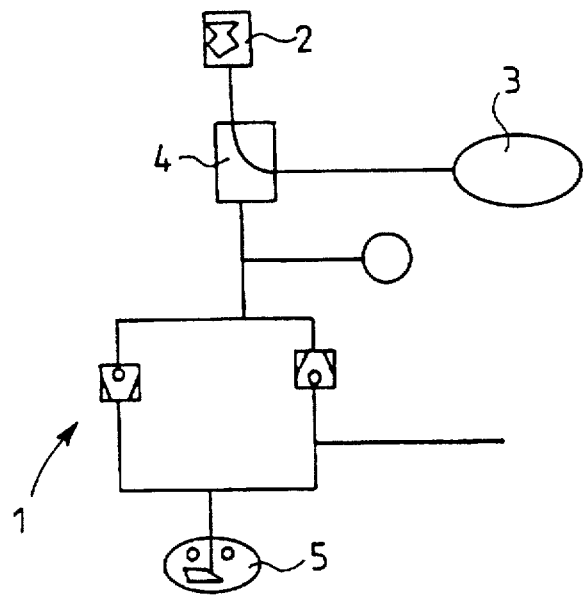

FIG. 11 shows an application in which the pressure or the flow is measured in the patient circuit 1. In addition, information on the function desired is required, for instance the compression of the reservoir bag 3 or the ventilator.

Figure 12:
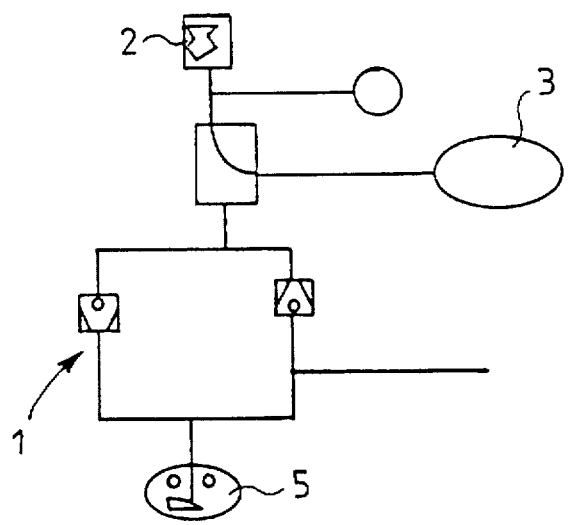

FIG. 12 shows an application in which the pressure or the flow is measured in the circuit associated with the ventilator 2. In addition, information on the function desired is required, for instance the compression of the reservoir bag 3.

The compression of the reservoir bag 3 can be measured in any suitable manner, for instance by different microswitch solutions, by solutions based on different detectors, the reservoir bag being thus provided with suitable pieces or the like, the movement or location of which is monitored by suitable sensors, etc.

The examples shown in the figures can naturally be provided with any equipment known as such, which gives an alarm signal after a faulty connection has been identified. The alarm signal may be for instance a light signal, a sound signal, a combination of a light signal and a sound signal, etc. The arrangement according to the invention may also be provided with an equipment which stops the operation after a faulty connection has been identified. These equipments represent known prior art to one skilled in the art, wherefore they are not described in more detail in this context.

The embodiments presented above are by no means intended to restrict the invention, but the invention may be freely modified within the scope of the claims. It will thus be apparent that different details of the invention may differ even to a great extent from the applications presented above, etc. The flow measurement may also be carried out in a manner other than by monitoring the pressure difference, for instance by means of a mass flow meter as stated above or by some other suitable measuring device.

We claim:

1. A method for use with equipment for ventilating a patient with breathing gas, the equipment having a mechanical ventilating part for supplying breathing gas, the mechanical ventilating part being connected to a switching valve, said valve comprising a single, unitary structure having first and second positions establishing first and second gas communication paths in the valve, the equipment having a manually operable part for supplying breathing gas and a patient circuit part for providing breathing gas to the patient, the manually operable part and the patient circuit part being connected to the valve, the manually operable part and the patient circuit part being capable of connection to the valve in a correct connection state in which breathing gas is supplied from the mechanical ventilating part to the patient circuit part when the valve is in a first position and from the manually operable part to the patient circuit part when the valve is in a second position, the manually operable part and the patient circuit part also being capable of being connected to the valve in an incorrect connection state, said method identifying the correctness of the connection state of the manually operable part and the patient circuit part to the valve and comprising the steps of:

moving the valve to one of the first and second positions to establish one of the first or second gas communication paths in the valve;

operating the mechanical ventilating part if the valve has been moved to the first position or the manually operable part if the valve has been moved to the second position;

sensing a gas property condition associated with a selected one of the gas communication paths;

comparing the sensed gas property condition with information corresponding to gas property conditions existing when the patient circuit part and manually operable part are correctly connected to the switching valve; and determining the correctness of the connection of the manually operable part and patient circuit part to the valve from the comparison of the gas property condition information obtained from said sensing and from the information corresponding to correct connection gas property conditions.

2. The method according to claim 1 wherein the sensed gas condition property is one of a gas pressure property or a gas flow property.

3. The method according to claim 2 wherein the sensed gas pressure property is gas pressure.

4. The method according to claim 2 wherein the sensed gas flow property is flow direction.

5. The method according to claim 2 wherein the sensed gas flow property is gas flow amount.

6. The method according to claim 2 wherein the manually operable part has an expandable gas bag and wherein the sensed gas pressure property is the volumetric condition of the bag.

7. The method according to claim 1 further defined as operating the mechanical ventilating part and as sensing a gas property condition existing in one of the manually operable part and the patient circuit part.

8. The method according to claim 1 wherein the sensing step is further defined as sensing the gas property condition existing in the manually operable part.

9. The method according to claim 1 further defined as sensing the operative state of the mechanical ventilating part and as carrying out the determining step responsive to the operative state of the mechanical ventilating part.

10. The method according to claim 2 wherein the sensed gas pressure property is a gas pressure difference existing in the valve.

11. The method according to claim 2 wherein the sensed gas pressure property is the relative magnitude of gas pressures existing at a pair of points spaced along the selected gas communication path, and hence the direction of pressure existing in the path.

12. A method for use with equipment for ventilating a patient with breathing gas, the equipment having a mechanical ventilating part for supplying breathing gas, the mechanical ventilating part being connected to a switching valve, said valve comprising a single, unitary structure having first and second positions establishing first and second gas communication paths in the valve, the equipment having a manually operable part for supplying breathing gas and a patient circuit part for providing breathing gas to the patient, the manually operable part and the patient circuit part being connected to the valve, the manually operable part and the patient circuit part being capable of connection to the valve in a correct connection state in which breathing gas is supplied from the mechanical ventilating part to the patient circuit part when the valve is in a first position and from the manually operable part to the patient circuit part when the valve is in a second position, the manually operable part and the patient circuit part also being capable of being connected to the valve in an incorrect connection state, said method identifying the correctness of the connection state of the manually operable part and the patient circuit part to the valve and comprising the steps of:

moving the valve to the first position to establish the first gas communication path in the valve;

operating the mechanical ventilating part;

sensing a gas property condition existing in one of the manually operable part and patient circuit part;

comparing the sensed gas property condition with information corresponding to a gas property condition found in the manually operable part or the patient circuit part when the manually operable part and patient circuit part are correctly connected to the valve, and determining the correctness of the connection of the manually operable part and patient circuit part to the valve from said comparison of the sensed gas property condition and the information corresponding to correct connection gas property conditions.

13. The method according to claim 12 wherein the sensed gas condition property is one of a gas pressure property or a gas flow property.

14. Apparatus for use with equipment for ventilating a patient with breathing gas, the equipment having a mechanical ventilating part for supplying breathing gas, the mechanical ventilating part being connected to a switching valve, said valve comprising a single, unitary structure having first and second positions establishing first and second gas communication paths in the valve, the equipment having a manually operable part for supplying breathing gas and a patient circuit part for providing breathing gas to the patient, the manually operable part and the patient circuit part being connected to the valve, the manually operable part and the patient circuit part being capable of connection to the valve in a correct connection state in which breathing gas is supplied from the mechanical ventilating part to the patient circuit part when the valve is in a first position and from the manually operable part to the patient circuit part when the valve is in a second position, the manually operable part and the patient circuit part also being capable of being connected to the valve in an incorrect connection state, said apparatus identifying the correctness of the connection state of the manually operable part and the patient circuit part to the valve and comprising:

means coupled to one of the manually operable part, patient circuit part, and mechanical ventilating part for sensing a gas property condition existing in at least one of said first and second gas communication paths;

comparison means for comparing a sensed gas property condition with information corresponding to gas property conditions existing when the patient circuit part and manually operable part are correctly connected to the switching valve; and determining means coupled to said comparison means for determining the correctness of the connection of the manually operable part and patient circuit part to the valve from the comparison of the gas property condition information obtained from said sensing means and from the information corresponding to correct connection of gas property conditions.

15. The apparatus according to claim 14 wherein said sensing means is further defined as sensing one of a gas pressure property or a gas flow property.

16. The apparatus according to claim 15 wherein said sensing means is further defined as sensing gas pressure.

17. The apparatus according to claim 15 wherein said sensing means is further defined as sensing gas flow direction.

18. The apparatus according to claim 15 wherein said sensing means is further defined as sensing gas flow amount.

19. The apparatus according to claim 15 wherein the manually operable part has an expandable gas bag and wherein said sensing means senses the volumetric condition of the bag.

20. The apparatus according to claim 14 wherein said sensing means is further defined as sensing a gas property condition existing in one of the manually operable part and the patient circuit part.

21. The apparatus according to claim 14 further defined as having means for ascertaining the operative state of one of mechanical ventilating part and manually operable part.

22. The apparatus according to claim 14 wherein said sensing means is further defined as sensing the gas property condition existing in the patient circuit part.

23. The apparatus according to claim 14 wherein said sensing means is further defined as sensing the gas property condition existing in the manually operable part.

24. The apparatus according to claim 15 wherein said sensing means is further defined as sensing a pressure difference existing in the valve.

25. The apparatus according to claim 15 wherein said sensing means is further defined as sensing the relative magnitude of gas pressures existing at a pair of points spaced along a selected gas communication path, and hence the direction of pressure existing in the path.

26. An apparatus for use with equipment for ventilating a patient with breathing gas, the equipment having a mechanical ventilating part for supplying breathing gas, the mechanical ventilating part being connected to a switching valve, said valve comprising a single, unitary structure having first and second positions establishing first and second gas communication paths in the valve, the equipment having a manually operable part for supplying breathing gas and a patient circuit part for providing breathing gas to the patient, the manually operable part and the patient circuit part being connected to the valve, the manually operable part and the patient circuit part being capable of connection to the valve in a correct connection state in which breathing gas is supplied from the mechanical ventilating part to the patient circuit part when the valve is in a first position and from the manually operable part to the patient circuit part when the valve is in a second position, the manually operable part and the patient circuit part also being capable of being connected to the valve in an incorrect connection state, said apparatus identifying the correctness of the connection state of the manually operable part and the patient circuit part to the valve when the valve is in the first position and the mechanical ventilating means is operated, said apparatus comprising:

means for sensing a gas property condition existing in one of the manually operable part and patient circuit part;

comparison means for comparing the sensed gas property condition with information corresponding to a gas property condition found in the manually operable part or patient circuit part when the manually operable part and patient circuit part are correctly connected to the valve; and means for determining the correctness of the connection of the manually operable part and patient circuit part to the valve from the comparison of the sensed gas property condition and said information corresponding to correct connection gas property conditions.

27. The apparatus according to claim 26 wherein the sensed gas property condition is one of a gas pressure property or a gas flow property.

* * * * *